United States Patent [19]

Sanford

[11] 4,250,255
[45] Feb. 10, 1981

[54] ASSAY METHOD FOR ISOENZYME ACTIVITY

[75] Inventor: Karl J. Sanford, Rochester, N.Y.

[73] Assignee: Eastman Kodak Company, Rochester, N.Y.

[21] Appl. No.: 814,770

[22] Filed: Jul. 11, 1977

[51] Int. Cl.$^3$ .......................... C12Q 1/48; C12Q 1/42; C12Q 1/32
[52] U.S. Cl. .......................................... 435/15; 435/4; 435/21; 435/26
[58] Field of Search ..................... 195/103.5 R; 435/4, 435/15, 21, 26

[56] References Cited

U.S. PATENT DOCUMENTS

| | | | |
|---|---|---|---|
| 3,326,777 | 6/1967 | Babson | 195/103.5 R |
| 3,388,044 | 6/1968 | Babson | 195/103.5 R |
| 3,907,642 | 9/1975 | Richmond | 195/62 |
| 3,992,158 | 11/1976 | Przybylowicz et al. | 195/103.5 R |
| 3,994,783 | 11/1976 | Rao et al. | 195/103.5 R |

Primary Examiner—David M. Naff
Attorney, Agent, or Firm—Arthur H. Rosenstein

[57] ABSTRACT

The activity of an isoenzyme in a sample is determined by assaying for the isoenzyme in the presence of a predetermined concentration of an ionic amphiphile having a hydrophilic and a hydrophobic portion that has a discriminating effect on the activity of the isoenzyme and determining the activity of the isoenzyme present in the sample.

11 Claims, No Drawings

ASSAY METHOD FOR ISOENZYME ACTIVITY

FIELD OF THE INVENTION

This invention relates to methods for differentiating isoenzymes and for determining the amount of an isoenzyme present in a sample. The invention particularly relates to the use of amphiphiles to specifically affect the activity of isoenzymes.

BACKGROUND OF THE INVENTION

Isoenzymes are enzymatically active proteins catalyzing the same reaction and occurring in the same species, but differing in certain of their physical-chemical properties. For example, lactate dehydrogenase (L-lactate:NAD oxidoreductase, EC 1.1.1.27; LDH) is a tetrameric enzyme having a molecular weight in the range of 140,000 depending on the source. The enzyme is coded by two structural genes producing two subunits (H and M) which combine to form the active tetrameric LDH enzyme. The permutations of H and M subunits in the active enzyme lead to five isoenzymes, e.g., $H_4$, $H_3M$, $H_2M_2$, $HM_4$ $L$ $and$ $M_4$. Currently, nomenclature for the LDH isoenzymes is based on their relative migration in an electric field, i.e., electrophoresis. The order of increasing migration rate toward the anode is $H_4 > H_3M > H_2M_2 > HM_3 > M_4$ and they are designated as $LD_1$, $LD_2$, $LD_3$, $LD_4$ and $LD_5$, respectively.

In recent years, a great deal of attention has focused on the diagnostic value of isoenzymes. Determinations of the serum levels of the isoenzymes of cholinesterase, amylase, creatine kinase, lactate dehydrogenase, alkaline phosphatase and hexosaminidase have been found to have clinical value. For example, the relative levels of these LDH isoenzymes in a patient's serum, in addition to the total LDH activity, is of diagnostic value. This importance is derived from the relative abundance of $LD_1$ and $LD_2$ isoenzymes in heart, kidney and erythrocytes, $LD_4$ and $LD_5$ in skeletal muscle and the liver, and $LD_3$ in the spleen, lungs, pancrease, thyroid, adrenal gland and lymph nodes. Necrosis of cells in damaged organs results in the release of their respective enzymes into the blood stream. Thus, detection and quantitation of the LDH isoenzymes can give information pertinent to location of damaged tissue, e.g., myocardial infarction, liver disorders, etc. Saifer et al, *Clinical Chemistry*, Vol. 21, No. 3, pp. 334–42 (1975), describe a study of the relationship of various serum levels of hexosaminidase isoenzymes to carriers of Tay-Sachs disease. Also, the level of the cardiac-muscle isoenzyme of creatine kinase in serum is useful in diagnosing cardiac infarction (D. W. Mercer, *Clinical Chemistry*, Vol. 20, No. 1, pp. 36–40 (1974)).

In general, three approaches have been used in the determination of isoenzyme levels. They involve physical-chemical, electrophoretic and immunochemical methods. Since a large number of literature references describe research with LDH isoenzymes, the following discussion will focus on LDH although the approaches are relevant to other isoenzymes as well.

Wrobleroski et al, *Annotations of the New York Academy of Science*, Vol. 94, p. 912 (1961), describe the use of thermal denaturation as a method for determining LDH isoenzymes, making use of the differential stability to heat of the isoenzymes. Emerson et al, *Journal of Clinical Pathology*, Vol. 18, p. 803 (1965), describe the selective inhibition of LDH isoenzymes with reagents such as urea and oxalate. Warburton et al, *Enzymologia*, Vol. 26, p. 125 (1963), and Warburton et al, *Nature*, Vol. 198, p. 386 (1963), describe the use of organic solvents to precipitate LDH isoenzymes. U.S. Pat. Nos. 3,388,044 and 3,326,777 and Bishop et al, *Proceedings of the National Academy of Science*, Vol. 69, p. 1761 (1972), describe the use of pyruvate and lactate to differentially inhibit LDH isoenzymes. Cawley et al, *American Journal of Clinical Pathology*, Vol. 45, p. 737 (1966), describe electrophoretic techniques for separation of LDH isoenzymes. Nisselbaum et al, *Journal of Biological Chemistry*, Vol. 236, p. 401 (1961), describe a method for inhibiting LDH isoenzymes using antisera to human heart and liver enzymes.

The procedures described above generally suffer various deficiencies. The physical-chemical procedures suffer from lack of suffient specificity. For instance, they do not adequately distinguish between heart LDH isoenzymes, i.e., $LD_1$ and $LD_2$, and muscle LDH isoenzymes, i.e., $LD_4$ and $LD_5$. In addition, the procedures are time-consuming and tedious. For instance, in the relative heat-stability test, samples of serum to which NADH is added are heated to 57° C. and 65° C. for 30 minutes, after which the remaining enzyme activity is compared with that of an unheated sample. The control gives total LDH, while the difference between the activities of the control and the sample at 57° C. gives a measure of the heat-labile enzyme, principally $LD_5$. The activity of the heat-stable fraction, ($LD_1$), is that of the sample heated at 65° C., while the difference between the activities of the two heated samples is an index of the $LD_2$, $LD_3$ and $LD_4$ isoenzymes. Although the information that one hopes to obtain is extremely useful, the temperature control, NADH concentration and protein concentration are parameters that affect the enzyme stability. Because these parameters are, in general, difficult to control, the results are not always reliable. However, this type of approach to isoenzyme assay is, in general, more rapid than electrophoretic procedures.

Electrophoretic methods suffer the disadvantage of being time-consuming and tedious. In addition to running the electrophoresis, the technician must also (1) prepare the reagents for the LDH reaction, and because such reagents are generally unstable, they must be prepared fresh for each run (2) incubate the electrophoresis plates after exposure to reagent solution, (3) apply a fixing wash to the samples and (4) make a densitometric reading. The entire operation may take a minimum of several hours and requires the attention of a technician. In addition, the staining procedure must be carefully controlled so as to prevent under- or overstaining which leads to erroneous results.

Immunochemistry has shown promise as a potential technique in the isoenzyme assay field. For instance, the use of LDH isoenzymes as antigens affords the production of antisera that are relatively specific discriminators among the isoenzymes. However, the production of active antibodies is elicited only when the native LDH enzyme is used as the antigen. If $LD_1$ is the antigen, antisera for $LD_1$ are produced with inhibitory effect on $LD_4 < LD_3 < LD_2$. Conversely, if $LD_5$ is used as the antigen, antisera specific for $LD_5$ are produced with inhibitory effect on $LD_2 < L_3 < L_4$. Moreover, there is evidence of nonneutralizing antibody formation which protects isoenzymes from antibody inactivation. Also, the production of antisera is time-consuming and its purification is difficult.

Thus, it can be appreciated that better ways for assaying isoenzymes are continuously being sought.

SUMMARY OF THE INVENTION

I have found that amphiphiles can specifically or differentially affect the activity of isoenzymes and thus provide a means for discriminating between the isoenzymes present in a sample. This invention provides a method of assaying for the isoenzymes present in a sample of biological origin. This method for determining the activity of an isoenzyme present in a sample comprises assaying for the isoenzymes in the presence of a predetermined concentration of an amphiphile that has a discriminating effect on the activity of the isoenzyme and determining the amount of isoenzyme present in the sample. The particular amphiphile and the concentration of the amphiphile used are determined based on the isoenzyme being assayed, the other isoenzymes present and the concentration of other proteins in the sample.

As used herein, the term "amphiphile" refers to an ionic compound that has a hydrophilic portion and a hydrophobic portion, for example, a surfactant.

DETAILED DESCRIPTION OF THE INVENTION

Surfactants have been widely used for the purification and characterization of proteins because of their solubilizing and dissociating properties. For instance, nonionic surfactants such as Triton X-100 (trademark of Rohm and Haas Co.) have been found useful in extracting enzymes from cells. Marganen et al, *Biochimica et Biophysica Acta*, Vol. 371, pp. 442–50 (1974), describe the use of the cationic surfactant cetyltrimethylammonium bromide in the polyacrylamide-gel electrophoresis of hydrophilic proteins to determine molecular weight. Jones et al, *Journal of Biochemistry*, Vol. 135, p. 231–6 (1973), describe the interaction between ribonuclease A and the two surfactants, sodium n-dodecylsulfate and n-dodecyltrimethylammonium bromide. To my knowledge, however, no one has described or suggested that amphiphiles such as surfactants could be used to discriminate between isoenzymes, and it is unexpected that amphiphiles would differentially affect the activity of isoenzymes.

In accord with the present invention, a method of assaying for an isoenzyme in a sample comprises performing the assay in the presence of a predetermined concentration of an amphiphile that has a discriminating effect on the activity of the isoenzyme. In a preferred embodiment, a predetermined concentration of the amphiphile specifically inhibits the activity of the isoenzyme being assayed. Thus, the activity of isoenzyme is determined by performing the assay procedure twice, once without the presence of the amphiphile and once in the presence of the amphiphile. The activity of the isoenzyme is the difference between the two assays. Of course, in an especially preferred embodiment, a predetermined concentration of amphiphile specifically inhibits the activity of all the isoenzymes except the particular isoenzyme being assayed. Thus, the activity of the desired isoenzyme can be determined directly by one assay procedure.

Any amphiphile that can discriminate the particular isoenzyme, i.e., differentially affect the activity of the isoenzyme, can be used in the assay procedure in accord with this invention. Useful such amphiphiles include, for example, heparin and ionic surfactants. Examples of ionic surfactants useful in the practice of this invention include hexadecyltrimethylammonium bromide, hexadecylpyridinium bromide, N-ethylpyridinium bromide, tetrapropylammonium bromide, nonatrimethylammonium bromide, dodecylamine hydrogen chloride, dodecyltrimethylammonium bromide, trioctylpropylammonium bromide, cetylpyridinium bromide, sodium dodecyldiphenylether disulfonate, sodium n-decyldiphenylether disulfonate, sodium isopropylnaphthalene sulfonate, dialkyl ester of sodium sulfosuccinic acid, disodium N-octadecylsulfosuccinamate, sodium N-methyl-N-oleoyl taurate, sodium octylphenolpoly(etheneoxy)sulfonate, sodium alkyl sulfonate, octylphenolpoly(1-oxapropene)oxaethene carboxylic acid sodium salt, dodecanoic acid sodium salt, perfluorooctyl carboxylic acid, perfluoroheptyl carboxylic acid, dehydrocholic acid sodium salt, sodium stearate, sodium butylsulfate, sodium octylsulfate, sodium decylsulfate, sodium dodecylsulfate, sodium tetradecylsulfate, $C_{7-8}$ fluoroalkylphosphate, lauric acid derivative of imidazole alkyl halide salt, oleic acid derivative of imidazole alkyl halide salt, tetradecyltrimethylammonium bromide, $C_{7-8}$ dimethylsulfate quaternary amine, perfluoro aromatic quaternary amines, etc.

Of course, the particular amphiphile used and the concentration at which it is used will depend upon the particular isoenzyme being assayed. Not every amphiphile will have a discriminatory effect on the activity of isoenzymes in each isoenzyme system. For instance, hexadecyltrimethylammonium bromide and sodium decylsulfate have been found to be excellent discriminators for LDH isoenzymes. However, these same two amphiphiles do not appear to have any discriminatory effect on the activities of the isoenzymes of creatinine phosphokinase (CPK), at least when assayed by a conventional assay procedure using coupled reactions and an assay solution containing hexokinase and glucose-6-phsophate dehydrogenase.

The following test is easily performed to determine whether an amphiphile will differently affect the activity of an isoenzyme. A series of solutions are prepared for each amphiphile covering a wide range of concentrations. Generally, a concentration range of from about 0.01 to about 100 mM should be sufficient. The activity of each isoenzyme is determined in the presence of the amphiphile and compared with its activity in buffer (without amphiphile) for each concentration of amphiphile in the series. A plot of relative activity against concentration will facilitate the determination of the concentration of amphiphile at which the maximum discrimination occurs.

As stated above, it is preferred to select amphiphiles that selectively inhibit an isoenzyme. However, this is not necessary to practice the present invention. It is only necessary to select amphiphiles that discriminate between isoenzymes by differentially affecting the activity of the isoenzymes. Consider, for example, a situation in which it is desired to assay for the isoenzymes $I_x$, $I_y$ and $I_z$ that are found in a sample. From assays with pure $I_x$, $I_y$ and $I_z$, it has been determined that, when assayed in the presence of 1.0 mM of amphiphile $A_1$, the activity of $I_x$ is inhibited 50%, the activity of $I_y$ is inhibited 75% and the activity of $I_z$ is unchanged. A total assay is conducted in the presence of 1.0 mM $A_1$, resulting in an activity of 650 U per liter. From this information, the following equation can be written:

$$0.5x + 0.25y + z = 650 \quad (1)$$

where x, y and z are the activities of the isoenzymes $I_x$, $I_y$ and $I_z$, respectively, found in the sample.

Again from assays with pure $I_x$, $I_y$ and $I_z$, it has been determined that, when assayed in the presence of 0.5 mM of amphiphile $A_2$, the activity of $I_x$ increases 25%, the activity of $I_y$ is inhibited 25% and the activity of $I_z$ is completely inhibited. A total assay is conducted in the presence of 0.5 mM $A_2$, resulting in an activity of 500 U per liter. From this information, the following equation can be written:

$$1.25x + 0.75y = 500 \quad (2)$$

Next, a total assay is conducted with no amphiphile present and an activity of 1000 U per liter is found. Therefore, the following equation can be written:

$$x + y + z = 1000 \quad (3)$$

The three equations above can now be solved simultaneously to determine the activity of each individual isoenzyme. In the hypothetical situation outlined above, the activities of the isoenzymes are determined as $I_x = 200$ U per liter, $I_y = 333$ U per liter and $I_z = 467$ U per liter. It should be obvious to those skilled in the art that any group of isoenzymes can be assayed in a manner similar to the above hypothetical situation used to illustrate the method of the present invention. In performing such an assay, one skilled in the art will recognize that one determination must be made for each isoenzyme present in the sample if it is desired to obtain the separate activity of each individual isoenzyme. It will also be recognized that the same amphiphile at two different concentrations can be used in place of two different amphiphiles, and that a determination with no amphiphile present can take the place of one determination with an amphiphile present. Thus, for purposes of this invention a different amphiphile can also mean a different concentration of the same amphiphile or no amphiphile at all.

In general, any conventional assay procedure for determining the activity of the isoenzyme of interest can be used in the method of the present invention. The methods for assaying isoenzymes described in the present invention are useful in conventional liquid assays. It should be readily apparent to the skilled artisan that all of the reagents may be provided in dry or lyophilized form and reconstituted with water immediately prior to use. Procedures using lyophilized reagents are clearly contemplated by this invention.

In addition, the methods described in the present invention are particularly useful when the analyte determination is performed in a multilayer element of the type described in U.S. Pat. No. 3,992,158, issued Nov. 16, 1976, in the names of Przybylowicz and Millikan, the disclosure of which is incorporated by reference. Elements of this type generally comprise:

(1) a spreading layer,
(2) a reagent layer that is in fluid contact with the spreading layer under the conditions of use and,
(3) optionally, a support.

Preferred elements of this type employ a nonfibrous spreading layer.

Multilayer elements useful in the practice of this invention may also include a registration layer, i.e., a layer which underlies the spreading and reagent layers, contains no interactive materials and serves only to receive dyes produced in the overlying layers. Such layers generally comprise a matrix permeable to the dye and, as desired, other adjuvants such as mordants, surfactants, etc., which may enhance the layers, and their arrangement in analytical elements are described in more detail in Belgian Pat. No. 831,660 published Jan. 23, 1976, in the name of P. Clement and entitled "Integral Element for Analysis of Liquids", the disclosure of which is hereby incorporated by reference.

The following examples are provided to illustrate further the use and advantages of the invention.

Examples 1-9 illustrate the differential affects of certain amphiphiles on the activities of LDH isoenzymes. Unless otherwise noted the following applies to Examples 1-9:

1. The amphiphiles were recrystallized from either ethanol-water or ethanol-acetone solutions and thoroughly dried in vacuo prior to use.

2. Distilled water passed through an ion-exchange column was used to prepare buffers and all other buffer-containing solutions.

3. Beef heart LDH (Sigma Chemical Co., Type III), rabbit muscle LDH (Sigma Chemical Co., Type V) and porcine LDH, $LD_1$, $LD_2$, $LD_3$, $LD_4$ and $LD_5$ in the form of ammonium sulfate suspensions were used for these examples.

4. The NADH used was a Grade III disodium salt isolated from yeast. The cofactor was stored as a powder under anhydrous conditions, at room temperature and protected from light.

5. Assay for LDH activity

The assay for LDH activity in both the absence and presence of surfactant was conducted as follows. Stock solutions of NADH (1.8 mM) and pyruvate (9.8 mM) were prepared fresh daily in 30 mM sodium phosphate buffer, pH 7.4. Enzyme solutions were prepared fresh daily by withdrawing 5 $\mu$l of the stock enzyme solutions with a Hamilton syringe and diluting to 5 ml with 30 mM phosphate buffer. The resulting solution contains approximately 5 units/ml. The enzyme assay was conducted by pipetting 2.7 ml of buffer or buffer-surfactant solution into a 10 mm quartz cuvette followed by 100 $\mu$l each of both the NADH and pyruvate stock solutions. The cuvette was placed in a thermostated cell holder and placed in a Cary 118 spectrophotometer and allowed to equilibrate for 1 minute at 25° C. To the equilibrated solution 100 ml. of the enzyme solution was added, and the cuvette was rapidly shaken while covering the top of the cuvette with a small piece of Parafilm ® and placed back into the spectrophotometer. The absorbance decrease at 340 nm was measured as a function of time. The rate of the reaction was determined by measuring the slope of the initial absorbance decrease, i.e., within the first 50 seconds of the reaction.

6. Amphiphile Stock Solution

Amphiphile solutions were prepared by weighing out a given amount of amphiphile, e.g., 100 mg, and preparing a stock solution in 30 mM sodium phosphate buffer in 100 ml. volumetric flask. Solutions of lower amphiphile concentration were prepared by making the appropriate dilutions from the stock solution.

EXAMPLE 1

Amphiphile Interaction with LDH Isoenzymes

The LDH enzyme assay (pyruvate+NADH→) is measured by the decrease in NADH absorbance at 340 nm with respect to time. In the presence of amphiphile, a highly specific inactivation of LDH isoenzymes occurs as shown in FIGS. 1A and 1B. In FIG. 1A the activity profile of $LD_5$ (rabbit muscle) in the presence of sodium decylsulfate (DSS), 8.65 mM, and cetylpyridinium bromide (CP), 1 mM, is illustrated. Clearly, the anionic detergent rapidly inactivates the $LD_5$ isoenzyme whereas, in the presence of the cationic detergent, almost no loss of activity is observed. The opposite is observed with $LD_1$ (beef heart) as illustrated in FIG. 1B. That is, complete inactivation of $LD_1$ occurs in the presence of CP (1B) whereas, in the anionic detergent, almost no loss in $LD_1$ activity is observed. Moreover, the specific inactivation of $LD_1$ and $LD_5$ by the cationic and anionic detergents, respectively, is rapid; i.e., complete inactivation took place within the dead time of the instrument (about 5 sec.).

EXAMPLE 2

Cationic Amphiphile Interaction with LDH Isoenzymes

A number of cationic amphiphiles were investigated for specific inactivation of $LD_1$ in the presence of $LD_5$ and these compounds are listed in Table 1.

TABLE 1

Effect of Cationic Amphiphiles on the Activity of LDH Isoenzymes

| Amphiphile | Amphiphile conc. Req'd for 50% Inactivation of Specified Isoenzyme |
|---|---|
| N-Ethylpyridinium bromide | no effect |
| Tetrapropylammonium bromide | no effect |
| Nonatrimethylammonium bromide | ($LD_5$) 0.15 mM |
|  | ($LD_1$) 0.35 mM |
| Dodecylamine . HCl | ($LD_5$) 6.5 mM |
|  | ($LD_1$) 13 mM |
| Dodecyltrimethylammonium bromide | ($LD_1$) 10 mM |
|  | ($LD_5$) 12 mM |
| Trioctylpropylammonium bromide | ($LD_1$) 1.6 mM |
|  | ($LD_5$) 2.2 mM |
| Hexadecylpyridinium bromide | ($LD_1$) 0.07 mM |
|  | ($LD_5$) 0.4 mM |
| Hexadecyltrimethylammonium bromide | ($LD_1$) 0.9 mM |
|  | ($LD_5$) > 10 mM |
| Dimethyldioctadecylammonium bromide | —* |
| Didodecyldimethylammonium bromide | —* |

*Not soluble in aqueous buffer

EXAMPLE 3

Effect of Cetylpyridinium Bromide (CP) on Activity of LDH Isoenzymes

The effect of CP on the LDH isoenzymes $LD_1$, $LD_2$, $LD_3$, $LD_4$ and $LD_5$ is illustrated in FIG. 2. The complete inactivation of all but $LD_5$ occurs at approximately the same amphiphile concentration, i.e., 0.1 mM. At this level of amphiphile, there is still 100% of $LD_5$ activity relative to a buffer control. However, an amphiphile concentration is increased. $LD_5$ activity is gradually lost. The behavior of $LD_1$ and $LD_5$ over a broader range of surfactant concentration is shown in FIG. 3. Several observations can be made. (1) At higher concentrations of CP, i.e., 1 mM, $LD_5$ activity is greatly reduced. (2) $LD_5$ from two different species, i.e., rabbit muscle and hog muscle, exhibits differential stability to CP inactivation with the hog muscle being more stable than the rabbit muscle enzyme. (3) After complete inactivation of $LD_5$ (rabbit muscle), further increases in CP concentration reduce the inactivation effect on $LD_5$. This effect on increasing CP concentration is not observed for $LD_1$.

EXAMPLE 4

Effect of Hexadecyltrimethylammonium Bromide on the Activity of LDH Isoenzymes

The effect of hexadecyltrimethylammonium bromide (CTAB) on the five LDH isoenzymes is shown in FIG. 4. The general behavior of the isoenzyme-detergent interaction is similar to that with CP. However, the inactivation of $LD_1$, $LD_2$, $LD_3$ and $LD_4$ occurs at a higher concentration of surfactant and there is a smaller degree of $LD_5$ inactivation.

The behavior of $LD_1$ and $LD_5$ (from rabbit and hog muscle) over a broad CTAB concentration range is given in FIG. 5. Several observations can be made. (1) Unlike with CP, $LD_5$ from rabbit and hog sources show almost identical inactivation profiles in the presence of CTAB. (2) No more than 30% of the control $LD_5$ activity is lost in CTAB solutions even at 10 mM solutions of surfactant. (3) $LD_1$ is apparently less susceptible to inactivation at high surfactant concentrations, i.e., about 10 mM.

EXAMPLE 5

Use of CTAB to Assay for $LD_5$ Isoenzyme in Solution

A solution containing all five LDH isoenzymes was assayed for varying concentrations of $LD_5$ with a 0.275 mM CTAB solution in 30 mM phosphate buffer, pH 7.4. The procedure involved assaying $LD_5$ in buffer, $LD_5$ in CTAB solution and then $LD_5$ in the presence of the other four LDH isoenzymes in CTAB solution. The results are shown in FIG. 6. A linear activity-$LD_5$ concentration curve is obtained for all three solution types, i.e., $LD_5$-buffer, $LD_5$-CTAB, $LD_5$+other isoenzymes - CTAB. Because the activity of $LD_5$ in CTAB is approximately 90–95% of the buffer value, the slightly depressed values for $LD_5$-CTAB and $LD_5$, $LD_4$, $LD_2$, $LD_1$-CTAB can be corrected for.

EXAMPLE 6

Use of CP to Assay for $LD_5$ Isoenzyme in Solution

An assay similar to Example 5 was conducted with CP as the amphiphile. The results are presented in FIG. 7. In the case of CP, approximately 30% $LD_5$ activity is lost in the assay; consequently, $LD_5$ activity in the $LD_5$-CP and $LD_5$, $LD_4$, $LD_3$, $LD_2$, $LD_1$-CP solutions is expected to be depressed relative to buffer values. This reduction in $LD_5$ activity is indeed observed; however, a linear activity-$LD_5$ concentration curve is obtained allowing for an effective $LD_5$ assay procedure.

EXAMPLE 7

Effect of Anionic Amphiphile on the Activity of LDH Isoenzymes

A number of anionic amphiphiles were investigated for specific inactivation of $LD_5$ in the presence of $LD_1$ and these compounds are listed in Table 2.

TABLE 2

Anionic Amphiphiles Tested for Specific Interaction with LDH Isoenzymes

| Amphiphile | Interaction |
|---|---|
| 1. butyl sulfate | no effect |
| 2. octyl sulfate | no effect |
| 3. dehydrocholic acid | no effect |
| 4. lauric acid | no effect |

TABLE 2-continued

| Anionic Amphiphiles Tested for Specific Interaction with LDH Isoenzymes | |
|---|---|
| Amphiphile | Interaction |
| 5. lithium stearate | no effect |
| 6. sodium decylsulfate | specific |
| 7. sodium dodecylsulfate | specific |

Of the anionic amphiphiles tested, sodium decylsulfate (DSS) and sodium dodecylsulfate (SDS) demonstrated useful positive results.

EXAMPLE 8

Effect of Sodium Decylsulfate and Sodium Dodecylsulfate on the Activity of LDH Isoenzymes Sodium decylsulfate (DSS) interaction with the five LDH isoenzymes is illustrated in FIG. 8. A clearly ordered sequence in the inactivation of the isoenzymes is observed. At a DSS concentration of 7 mM, all the $LD_5$ and $LD_4$ activity is destroyed, leaving roughly 30% $LD_3$, 60% $LD_2$ and 65% $LD_1$ relative to buffer activities. Beyond 9 mM amphiphile, only $LD_1$ continues to show activity. Hence, an assay yielding information on the $LD_1$ and $LD_2$ levels could be obtained using DSS as a reagent.

The interaction of LDH isoenzymes with SDS is shown in FIG. 9. As compared with DSS effects, SDS is a more potent inactivator; i.e., inactivation of all the isoenzymes occurs at a lower amphiphile concentration, and the SDS system seemingly provides a more specific assay for $LD_1$; i.e., at 3.5 mM SDS $LD_2$ activity is 0, whereas $LD_1$ activity is 78% of buffer control. It is interesting to note that at 1.5 mM SDS, $LD_4$ and $LD_5$ activities are nil, whereas 50% $LD_3$, 65% $LD_2$ and 95% $LD_1$ activities remain. Thus, it is possible through proper selection of SDS concentration to assay for $LD_1$, or $LD_1$, $LD_2$ and $LD_3$ activities in the presence of the other LDH isoenzymes.

EXAMPLE 9

Use of DSS to Assay for $LD_1$ Isoenzyme in Solution

A solution containing all five LDH isoenzymes was assayed for varying concentrations of $LD_1$ with 9 mM DSS solution in 30 mM phosphate buffer, pH 7.4. The experimental protocol was similar to that described in Examples 5 and 6 and the results are presented in FIG. 10. Several observations may be made. (1) The activity-$LD_1$ concentration profile is linear. (2) There is a slight elevation of $LD_1$ in the presence of other enzymes in detergent solution relative to $LD_1$ alone in detergent solution. This increased activity is presumably due to $LD_2$ activity. (3) As expected, the $LD_1$ activity in amphiphile solution is less than control $LD_1$ activity in buffer due to $LD_1$ inactivation by the amphiphile. (4) An accurate procedure has been developed for the assay of $LD_1$ activity in the presence of the other four LDH isoenzymes.

EXAMPLE 10

Screening of Amphiphiles for Ability to Discriminate Between $LD_1$ and $LD_5$

A series of solutions was prepared covering a range of concentrations for each amphiphile to be tested. The activities of both $LD_1$ and $LD_5$ were determined in the presence of the various concentrations of each amphiphile and compared with enzyme activities in buffer (relative activity). Table 3 reports the results showing the effectiveness of the amphiphiles tested for the selective inhibition of $LD_1$ and $LD_5$.

Enzyme activity in the presence and absence of amphiphile was measured by the following procedure: Stock solutions of NADH (4 mM) and pyruvate (40 mM) were prepared daily in 30 mM sodium phosphate buffer, pH 7.4. Enzyme solutions were prepared daily by withdrawing 5 µl of the stock enzyme solutions with a Hamilton syringe and diluting to 5 ml with 30 mM sodium phosphate buffer. (The resulting solution contains approximately 5 U of enzyme/ml.) The enzyme assay was run by pipetting 2.7 ml of buffer or buffer surfactant solution into a 10 mm path length quartz cuvette, and 100 µl each of NADH and pyruvate stock solutions were added. The cuvette was placed in a thermostated cell holder in a Cary 118 spectrophotometer and allowed to equilibrate for one minute at 25° C. Enzyme solution was added with good mixing; the absorbance decrease at 340 nm was measured as a function of time. The rate of the reaction was determined by measuring the slope of the initial absorbance decrease, i.e., within the first 50 seconds of the reaction.

TABLE 3

| Amphiphiles Screened for LDH Isoenzyme Inhibition Specificity | |
|---|---|
| Amphiphile | Effectiveness |
| 1. Sodium n-decyldiphenylether disulfonate (Dowfax ® 3B2) | ++ |
| 2. Sodium isopropylnaphthalene sulfonate (Aerosol ® $O_1S$) | + |
| 3. Dialkyl ester of sodium sulfosuccinic acid (Aerosol ® 196) | 0 |
| 4. Sodium N-methyl-N-oleoyl taurate (Igepon ®) | 0 |
| 5. Disodium N-octadecylsulfosuccinamate (Aerosol ® 18) | ++ |
| 6. Sodium octylphenolpoly(etheneoxy) sulfonate (Triton ® X-200, purified to remove alcohols) | -- |
| 7. Alkyl sulfonate (Monflor ® 31) | ++ |
| 8. octylphenolpoly(1-oxapropene)oxaethane carboxylic acid sodium salt (Akypo ® OP-115, sodium salt) | 0 |
| 9. Sodium dodecanoate | 0 |
| 10. $C_{7-8}$ perfluoroalkylcarboxylic acid (Zonyl ® FSA) | ++ |
| 11. Sodium dehydrocholate | 0 |
| 12. Sodium stearate | 0 |
| 13. *Sodium butyl sulfate | 0 |
| 14. *Sodium octyl sulfate | + |
| 15. *Sodium decylsulfate | ++ |
| 16. *Sodium dodecylsulfate | ++ |
| 17. *Sodium tetradecylsulfate | ++ |
| 18. Heparin | + |
| 19. $C_{7-8}$ perfluoroalkylphosphate (Zonyl ® FSP) | 0 |
| 20. Oleic acid derivative of imidazole alkyl halide salt (Amine ® 0) | − |
| 21. Lauric acid derivative of imidazole alkyl halide salt (Amine ® C) | − |
| 22. Nonatrimethylammonium bromide | − |
| 23. *Dodecyltrimethylammonium bromide | − |
| 24. *Tetradecyltrimethylammonium bromide | −− |
| 25. *Hexadecyltrimethylammonium bromide | −− |
| 26. *Hexadecylpyridinium bromide | −− |
| 27. *Dodecylamine hydrogen chloride | ++ |
| 28. *Trioctylpropylammonium bromide | 0 |
| 29. N-β-hydroxyethyl-N,N-dimethyl-N-3-palmitamidopropylammonium chloride | ++ |
| 30. Tetrapropylammonium bromide | 0 |
| 31. $C_{7-8}$ perfluorodimethylsulfate | − |

TABLE 3-continued

Amphiphiles Screened for LDH Isoenzyme Inhibition Specificity

| Amphiphile | Effectiveness |
|---|---|
| quaternary amine (Zonyl ® FSC) | |

*Surfactants were recrystallized at least once before interaction with LDH was determined.
++ Specific inhibition of $LD_5$ relative to $LD_1$.
+ Partial selective inhibition of $LD_5$ relative to $LD_1$.
0 No selective inhibition of $LD_1$ or $LD_5$.
− Partial selective inhibition of $LD_1$ relative to $LD_5$.
− − Specific inhibition of $LD_1$ relative to $LD_5$.

Trademark Identification

| | | |
|---|---|---|
| 1. | Dowfax ® | The Dow Chemical Company |
| 2. | Aerosol ® | American Cyanamid Company |
| 3. | Igepon ® | GAF Corporation |
| 4. | Triton ® | Rohm & Haas Company |
| 5. | Monflor ® | Imperial Chemical Industries |
| 6. | Akypo ® | Chem-Y Corp. (Holland) |
| 7. | Zonyl ® | E. I. du Pont de Nemours & Co. |
| 8. | Amine ® | Ciba-Geigy Chemical Corporation |

Several nonionic surfactants were briefly studied with LDH, and no selective inactivation of isoenzymes was observed up to 2% w/v solutions.

EXAMPLE 11

Effect of N-β-Hydroxyethyl-N,N-dimethyl-N-3-palmitamidopropylammonium Chloride on the Activity of LDH Isoenzymes Unlike other cationic amphiphiles studied, which usually completely inactivate $LD_1$–$LD_4$ leaving only $LD_5$ activity, N-β-hydroxyethyl-N,N-dimethyl-N-3-palmitamidopropylammonium chloride inactivated mostly $LD_1$–$LD_3$ leaving high retention of $LD_5$ activity (90%) and ~60% $LD_4$ as shown in FIG. 11. Thus, an assay for $LD_5$ and $LD_4$ is possible, and when coupled to an $LD_5$ assay would allow estimation of $LD_4$.

EXAMPLE 12

Effect of Heparin on the Activity of LDH Isoenzymes

An unexpected result was obtained from heparin, a sulfated mucopolysaccharide. Heparin effects LDH activity in a fashion opposite that predicted on the basis of the study made on other sulfate moiety-containing polyanions; $LD_1$ is more inactivated than $LD_5$, as shown in FIG. 12.

The following Examples 13–17 illustrate the use of the methods of the present invention with human LDH isoenzymes. In Examples 13–17, the following applies:

7. Preparation of Human Enzyme-Containing Serum

Pooled human serum, kept frozen until ready for use, was raised to pH 11.5 until all LDH activity was destroyed. The pH was then adjusted to 7.4 and the serum was again assayed for LDH activity to ensure that no LDH had been reactivated. A specific human LDH isoenzyme (obtained from liver homogenate or red blood cell) was then added to the pool to give an enzyme concentration of ~100 U/l. The spiked serum samples were refrigerated between uses and respiked when necessary. Fresh serum was prepared weekly.

8. The assay method used is the same as described above for Examples 1–12, except that the test samples consisted of 25–30 μl of serum instead of 100 μl of aqueous enzyme solution.

EXAMPLE 13

Effect of CTAB on the Activity of Human LDH Isoenzymes

The assay procedure described above, using varying concentrations of CTAB as the amphiphile and 25 μl serum samples, was used to demonstrate the differential inactivation of human serum LDH isoenzymes. As shown in FIG. 13, the sample containing isoenzymes $LD_1$, $LD_2$ and $LD_3$ is completely inactivated while that containing $LD_5$ retains at least 60% activity over the surfactant range of 0.002–0.004 M. ($LD_4$ was not included in these samples.)

EXAMPLE 14

Effect of High Protein Concentrations on the Assay of Human LDH Isoenzymes

When adding high levels of protein (8–16%) to the amphiphile assay solution, the required amount of amphiphile remains normal (~3.0 mM). Moreover, in the presence of high protein concentration, the relative activity of the isoenzyme ($LD_5$ in this case) was greatly increased (>100%) while $LD_{1-3}$ remained completely deactivated. See FIG. 14.

EXAMPLE 15

Effect of pH on the Discrimination between Human $LD_5$ and $LD_4$ Isoenzymes

The solution assay, routinely run at pH 7.4, showed inadequate discrimination between $LD_5$ and $LD_4$ when CTAB was used as the amphiphile at this pH (see FIG. 15). It was found, however, that an amphiphile assay solution having a higher pH produced excellent differentiation between the isoenzymes.

A series was run with 30 μl serum samples containing both $LD_5$ and $LD_4$ using an amphiphile assay solution containing 3 mM CTAB in 14% protein. The pH of the reagent was varied from 7.3 to 8.3. FIG. 15 shows the optimum pH for differentiating between $LD_5$ and $LD_4$ to be 7.75–7.85; $LD_5$ was activated above 100% while $LD_4$ was completely inactivated.

EXAMPLE 16

Effect of CTAB Concentration of Human LDH Isoenzyme Discrimination

One optimized assay procedure, i.e., an amphiphile assay solution having pH 7.8 and containing 14% protein, was used to determine the effects of varying concentrations of CTAB on the isoenzymes. It was found that a solution containing 2.5 mM CTAB left $LD_4$ and $LD_5$ fully active, while $LD_1$ and $LD_2$ were completely inactivated.

EXAMPLE 17

Effect of DSS on the Activity of Human LDH Isoenzymes

The optimized assay procedure described above was used with 0.1 M sodium decylsulfate (DSS) as amphiphile. This solution completely deactivated $LD_{2,3,4}$ and 5 and left $LD_1$ fully active. These results using human sera correlate well with those in which ammonium sulfate suspensions of animal LDH were used.

Examples 18–21 illustrate the practice of the present invention in determining the isoenzymes of malate dehydrogenase (MDH). Malate dehydrogenase (L-malate:$NAD^+$ oxidoreductase, EC 1.1.1.37, MDH), a constituent of the citric acid cycle, is found in animals, plants and microorganisms. Although there has been a great deal of controversy regarding the actual number of MDH isoenzymes, recent studies have shown that two distinct isoenzymes exist in mammals, one located in the mitochrondria (mMDH) and the other in the cytoplasm (cMDH). Unless otherwise stated, the following applies to Examples 18–21:

1. Porcine cMDH and mMDH were used as ammonium sulfate suspensions. Typically, 5 μl of the enzyme stock solutions were diluted to 10 ml with 30 mM phosphate buffer, pH 7.4, prior to use. The resulting enzyme solutions were stored in ice water; 100 μl aliquots were withdrawn for assay except where another amount is specified.

2. Assay for MDH

The assay is based on conversion of oxalacetic acid to malate in the presence of NADH and MDH. The assay was made

$$H^+ + OAA + NADH \xrightarrow{MDH} Malate + NAD^+$$

in 30 mM phosphate buffer, at ambient temperature, with and without appropriate surfactant concentrations, and contained 0.17 mM OAA and 0.13 mM NADH. The reaction was followed by monitoring the decrease in absorbance at 340 nm using either a Beckman 25 or Cary 118 spectrophotometer. The OAA solutions were stored over ice to prevent hydrolysis to pyruvic acid.

EXAMPLE 18

Effect of CTAB on the Activity of MDH Isoenzymes

Using the assay procedure described above, various concentrations of CTAB (shown in FIG. 16) were added as the cationic amphiphile and the initial reaction rates were measured. As shown in FIG. 16, good resolution of the two isoenzymes is obtained; cMDH is essentially completely inactivated at 0.3 mM CTAB while mMDH retains 100% activity relative to a buffer control.

As the concentration of amphiphile is increased (>3.5 mM), resolution is decreased as mMDH begins to inactivate and cMDH appears to resist further inactivation.

EXAMPLE 19

Effect of DSS on the Activity of MDH Isoenzymes

The same procedure as in Example 18 was followed except that anionic amphiphile sodium decylsulfate (DSS) was used. There is a clear preferential inactivation of mMDH relative to cMDH as shown in FIG. 17.

EXAMPLE 20

Improved Discrimination Between MDH Isoenzymes

The same procedure as described in Example 18 was followed, except that rate measurements were made after 2 minutes rather than initially. Better resolution of the two MDH isoenzymes was obtained as illustrated in FIG. 18. It is noted that increasing the exposure time of the enzyme to CTAB more effectively inactivates cMDH with no effect on mMDH.

EXAMPLE 21

Effect of Amphiphiles on MDH Isoenzymes Added to Pooled Human Serum

To investigate the effect of serum proteins on the interaction of amphiphiles with MDH isoenzymes, pooled human serum was placed through a 1.5-meter AMP-Sepharose ® column to remove residual MDH and the resulting serum was spiked with porcine cMDH or mMDH. The assay procedure was identical to that described earlier using CTAB as the amphiphile except that the enzyme sample size was reduced to 20 μl to reduce protein-surfactant interference. FIG. 19 shows the activity profile obtained at 2 minutes. Increased resolution was obtained at 3 minutes, as shown in FIG. 20.

Examples 22–24 illustrate the use of the invention in assaying for isoenzymes of alkaline phosphatase, aspartate aminotransferase (SGOT) and creatinine phosphokinase.

EXAMPLE 22

Effect of Amphiphiles on Isoenzymes of Alkaline Phosphatase

The effect of amphiphiles on the isoenzymes of alkaline phosphatase was investigated using intestinal alkaline phosphatase (source: chicken) and liver alkaline phosphatase (source: beef). Assay for alkaline phosphatase activity was conducted using 30 mM glycine buffer at a pH of 8.5 with 1 mM p-nitrophenylphosphate as substrate. FIG. 21 shows the results of assaying the alkaline phosphatase isoenzymes in the presence of sodium dodecylsulfate. FIG. 22 shows the results of assaying for alkaline phosphatase isoenzymes in the presence of cetylpyridinium bromide with and without sodium chloride. Note the presence of 0.2 M sodium chloride significantly accentuates the discrimination between the isoenzymes.

EXAMPLE 23

Effect of Amphiphiles on Isoenzymes of Aspartate Aminotransferase

Aspartate aminotransferase (L-aspartate; 2-oxoglutarate aminotransferase EC 2.6.1.1) has been shown to contain at least two distinct isoenzymic forms. One isoenzyme is isolated from the cytoplasm and the other from the mitochondria. The isoenzymes of SGOT used for this example were contained in a lyophilized human-serum matrix and were stored at 4° C. and reconstituted with deionized water for use.

The assay used for SGOT was adapted from Henry et al, *American Journal of Clinical Pathology*, Vol. 34, p. 381 (1960), and Rodgerson et al, *Clinical Chemistry*, Vol. 20, p. 43 (1974). The assay solution contained 90 mM phosphate buffer, pH 7.4, 0.18 mM NADH, 6 mM 2-oxoglutarate, 125 mM aspartate and 4 units of MDH. The assay was conducted at 30° C. on a Beckman 25 spectrophotometer and the decrease in absorbance at 340 nm was monitored. Surfactant solutions were prepared in 90 mM phosphate buffer and used in place of assay buffer to determine the effect on the isoenzymes.

FIG. 23 shows the results of assaying for SGOT isoenzymes in the presence of hexadecyltrimethylammonium bromide (CTAB). FIG. 24 shows the results of assaying for SGOT isoenzymes in the presence of sodium decylsulfate (DSS). Cetylpyridinium bromide was also used but did not appear to discriminate between these isoenzymes.

EXAMPLE 24

The Use of Amphiphiles to Effect the Activity of Isoenzymes in an Assay Using a Multilayer Element Analytical elements containing all of the reagents necessary to quantitate specific isoenzymes were prepared according to the following format:

| Layer 2 | Spreading-Reagent Layer | Avicel ® spreading layer containing pyruvate and surfactant |
|---|---|---|
| Layer 1 | Reagent Layer Support | Agarose layer containing Tris buffer + NADH Lexan Support |

Using sodium decylsulfate to differentiate between $LD_1$ and $LD_5$ isoenzymes in an assay using a multilayer element, web structures were coated as follows:

A polycarbonate-subbed Lexan ® support was coated with a reagent layer comprising agarose (2.7 g/m$^2$) and NADH (0.12 g/m$^2$) in 0.1 M Tris buffer at pH 7.4, and a spreading-reagent layer comprising Avicel ® (43 g/m$^2$), sodium pyruvate (0.5 g/m$^2$), polyvinyl pyrrolidone (PVP) (2.15 g/m$^2$) in isopropyl alcohol, and sodium decylsulfate (DSS) (0.54 g/m$^2$).

Control webs were coated as above except no sodium decylsulfate was added to the spreading-reagent layer.

The webs were evaluated according to the following procedure:

Two aqueous solutions of purified porcine LDH isoenzymes, one containing $LD_1$ and the other $LD_5$, were prepared in 0.01 M Tris buffer, pH 7.4, at approximately 90 mU/ml. Sample aliquots (10 μl) of each solution and a buffer control (0.01 M Tris) were spotted onto the webs which were then monitored in a POS unit for decreasing fluorescence of the NADH with respect to time at 340 nm.

The control webs, i.e., with no surfactant, showed activities for $LD_1$ and $LD_5$ as shown in Table 4, whereas the test web containing surfactant DSS showed activity for $LD_1$ but no activity for $LD_5$; i.e. there was total inhibition of the activity of $LD_5$ in the presence of an anionic amphiphile.

TABLE 4

| Web | Isoenzyme Activity | |
|---|---|---|
| | $LD_1$ | $LD_5$ |
| control | 11 | 13 |
| DSS | 15 | 0 |

Those skilled in the art will readily appreciate that, when assaying for isoenzymes in accord with the methods described herein, wherever it is desirable to use a second amphiphile, one may also use the same amphiphile at a second predetermined concentration to accomplish an equivalent result.

The invention has been described in detail with particular reference to certain preferred embodiments thereof, but it will be understood that variations and modifications can be effected within the spirit and scope of the invention.

I claim:

1. A method for determining the activity of an isoenzyme in a sample, said method comprising:

performing a first assay to determine total enzyme activity in the sample;

performing a second assay in the presence of a predetermined concentration of an ionic amphiphile having a hydrophilic and a hydrophobic portion that specifically inhibits said isoenzyme; and determining the activity of said isoenzyme present in the sample, using the difference between the first and second assays.

2. The method of claim 1 wherein said isoenzyme is selected from the group consisting of isoenzymes of maleate dehydrogenase, alkaline phosphatase, and aspartate aminotransferase.

3. A method for determining the activity of an lactate dehydrogenase isoenzyme in a sample, said method comprising:

performing a first assay to determine total enzyme activity in the sample;

performing a second assay in the presence of a predetermined concentration of an ionic amphiphile having a hydrophilic and a hydrophobic portion that specifically inhibits said isoenzyme; and determining the activity of said isoenzyme present in the sample, using the difference between said first and second assays.

4. The method for determining the activity of an lactate dehydrogenase isoenzyme as described in claim 3 wherein said isoenzyme is $LD_1$ and said ionic amphiphile is selected from sodium decylsulfate or sodium dodecylsulfate.

5. The method for determining the activity of an lactate dehydrogenase isoenzyme as described in claim 3 wherein said isoenzyme is $LD_5$ and said ionic amphiphile is selected from cetylpyridinium bromide or hexadecyltrimethylammonium bromide.

6. The method for determining the activity of an lactate dehydrogenase isoenzyme as described in claim 3 wherein said ionic amphiphile is selected from the group consisting of heparin, sodium n-decyldiphenylether disulfonate, sodium isopropylnaphthalene sulfonate, disodium N-octadecylsulfosuccinamate, sodium octylphenolpoly-(etheneoxy)sulfonate, alkyl sulfonate, perfluoroalkylcarboxylic acid, sodium octylsulfate, sodium decylsulfate, sodium dodecylsulfate, sodium tetradecylsulfate, oleic acid derivative of imidazole alkyl halide salt, lauric acid derivative of imidazole alkyl halide salt, nonatrimethylammonium bromide, dodecyltrimethylammonium bromide, tetradecyltrimethylammonium bromide, hexadecyltrimethylammonium bromide, hexadecylpyridinium bromide, dodecylamine hydrogen chloride and perfluorodimethylsulfate quaternary amine.

7. A method for determining the activity of each of more than one isoenzyme in a sample, said method comprising:

quantifying the effect on the activity of each of said isoenzymes of different ionic amphiphiles having a hydrophilic and a hydrophobic portion or varying concentrations of a single ionic amphiphile having a hydrophilic and a hydrophobic portion which differentially affect the activity of each of said isoenzymes;

assaying in the presence of varying concentrations of a single said ionic amphiphile or different said ionic amphiphiles for concentrations of each isoenzyme by determining the concentration of each isoenzyme in relation to the other isoenzymes and determining the total concentration of isoenzymes and generating a number of equations containing a number of unknowns both of said number of equations and unknowns equal to the number of isoenzymes whose activity is to be determined; and solving said equations to determine the activity of each of said isoenzymes in said sample.

8. A method for determining the activity of n isoenzymes, wherein n is an integer more than one, in a sample, said method comprising:

quantifying the effect on the activity of each of said isoenzymes of different ionic amphiphiles having a hydrophilic and a hydrophobic portion or varying concentrations of a single ionic amphiphile having a hydrophilic and a hydrophobic portion which differentially affect each of said n isoenzymes;

assaying n times for concentration of each isoenzyme and for total concentration of isoenzymes in the presence of n predetermined concentrations of a single said ionic amphiphile or different said ionic amphiphiles to generate n equations in n unknowns; and solving said n equations in n unknowns to determine the activity of each of said n isoenzymes in said sample.

9. The method of claim 8 wherein said isoenzyme is selected from the group consisting of isoenzymes of lactate dehydrogenase, maleate dehydrogenase, alkaline phosphatase, and aminotransferase.

10. The method of claim 8 wherein said isoenzymes are isoenzymes of lactate dehydrogenase.

11. The method of claim 10 wherein said ionic amphiphile is selected from the group consisting of heparin, sodium n-decyldiphenylether disulfonate, sodium isopropylnaphthalene sulfonate, disodium N-octadecylsulfosuccinamate, sodium octylphenolpoly(etheneoxy)sulfonate, alkyl sulfonate, perfluoroalkylcarboxylic acid, sodium octylsulfate, sodium decylsulfate, sodium dodecylsulfate, sodium tetradecylsulfate, oleic acid derivative of imidazole alkyl halide salt, lauric acid derivative of imidazole alkyl halide salt, nonatrimethylammonium bromide, dodecyltrimethylammonium bromide, tetradecyltrimethylammonium bromide, hexadecyltrimethylammonium bromide, hexadecylpyridinium bromide, dodecylamine hydrogen chloride, and perfluorodimethylsulfate quaternary amine.

* * * * *